United States Patent [19]

Burdeska et al.

[11] Patent Number: 4,937,349
[45] Date of Patent: Jun. 26, 1990

[54] PROCESS FOR THE PREPARATION OF 3-[2'H-BENZOTRIAZOL-(2')-YL]-4-HYDROXY-BENZENESULFONIC ACIDS AND THE SALTS THEREOF

[75] Inventors: Kurt Burdeska, Basel; Otto R. Göttel, Marly, both of Switzerland

[73] Assignee: Ciba-Geigy Corporation, Ardsley, N.Y.

[21] Appl. No.: 259,565

[22] Filed: Oct. 19, 1988

[30] Foreign Application Priority Data

Oct. 29, 1987 [CH] Switzerland .............. 4230/87

[51] Int. Cl.$^5$ .............................. C07D 279/20
[52] U.S. Cl. .................................... 548/260
[58] Field of Search .............. 260/686, 505 A, 505 E; 548/260

[56] References Cited

U.S. PATENT DOCUMENTS 4,770,667 9/1988 Evans et al. .............. 8/128.1
4,775,386 10/1988 Reinert et al. .............. 348/260

FOREIGN PATENT DOCUMENTS 112120 6/1984 European Pat. Off.
1396107 6/1975 United Kingdom.

OTHER PUBLICATIONS

Australian Journal of Chemistry vol. 38, 1985 pp. 1163–1176.
Journal of the Chemical Society Perkin Transactions II (1985) pp. 677–682.
J. Chem. Soc. Perkin Trans II 1975, 1438–1445.

Primary Examiner—Donald G. Daus
Attorney, Agent, or Firm—Kevin T. Mansfield

[57] ABSTRACT

There is disclosed a process for the preparation of 3-[2'H-benzotriazol-(2')-yl]-4-hydroxybenzenesulfonic acids and salts thereof of formula

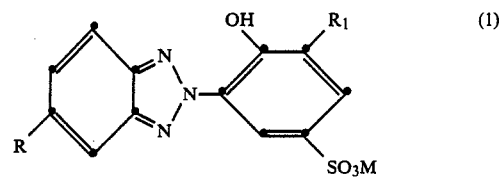

wherein
R is hydrogen or chlorine,
$R_1$ is branched or straight chain $C_1$-$C_{12}$alkyl or phenyl-$C_1$-$C_3$alkyl, and
M is hydrogen sodium or potassium, which process comprises sulfonating a 2-(2'-hydroxy-5'-tert-butylphenyl)-benzotriazole of formula

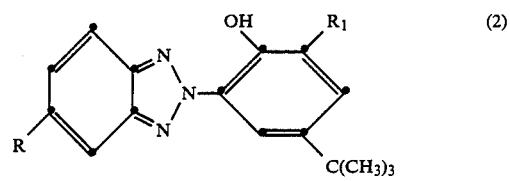

wherein R and $R_1$ are as defined above, and neutralizing the final product to pH 7. In the sulfonation, the tert-butyl group is replaced by the —$SO_3H$ group with elimination of isobutylene.

5 Claims, No Drawings

PROCESS FOR THE PREPARATION OF 3-[2'H-BENZOTRIAZOL-(2')-YL]-4-HYDROXY-BENZENESULFONIC ACIDS AND THE SALTS THEREOF

The present invention relates to a process for the preparation of 3-2'H-benzotriazol-(2')-yl]-4-hydroxybenzenesulfonic acids and the salts thereof.

Sodium salts of 3-2'H-benzotriazol-(2')-yl]-4-hydroxybenzenesulfonic acids are disclosed, for example, in European patent application 0 112 120. They are prepared by sulfonating corresponding 2-[2'H-benzotriazol-(2')-yl]phenols with chlorosulfonic acid, which starting materials are prepared in accordance with the process described by J. Rosevear and J. F. K. Wilshire, Aust. J. Chem. 1985, 38,1163–1176. Especially the preparation of the starting materials required for the synthesis of 3-[2'H-benzotriazol-(2')-yl]-4-hydroxybenzenesulfonates has proved to be difficult and uneconomic (q.v. loc. cit., page 1169, compound D).

A process has now been found which makes it possible to prepare 3-[2'H-benzotriazol-(2')-yl]-4-hydroxybenzenesulfonic acids and the salts thereof in simple manner and in very good yields.

The process of this invention for the preparation of 3-[2'H-benzotriazol(2')-yl]-4-hydroxybenzenesulfonic acids and the salts thereof of formula

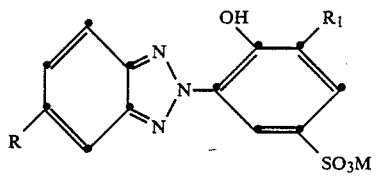

wherein
R is hydrogen or chlorine,
$R_1$ is branched, or straight chain $C_1$–$C_{12}$alkyl or phenyl-$C_1$–$C_3$alkyl, and
M is hydrogen, sodium or potassium, comprises sulfonating a 2-(2'-hydroxy-5'-tert-butylphenyl)benzotriazole of formula

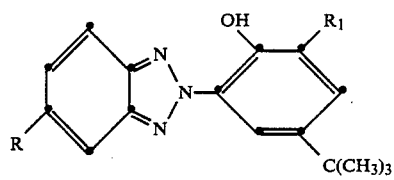

wherein R and $R_1$ are as defined above, with sulfuric acid, in which reaction the tert-butyl group is replaced by the —$SO_3H$ group with elimination of isobutylene, and neutralising the final product to pH 7.

The sulfuric acid required for the sulfonation can be 8–100%, preferably 96–100%, sulfuric acid or, preferably, oleum having a content of up to 25% of free $SO_3$.

The reaction temperatures can vary within wide ranges, for example from 0° to 200° C. When using sulfuric acid monohydrate, the preferred temperature range is from 70° to 100° C., in particular from 80° to 90° C. If, on the other hand, 25% oleum is used, the temperature range will be from 10° to 30° C. The reaction may be carried out under slightly reduced pressure, for example 146–187 mbar.

$R_1$ as branched or straight chain $C_1$–$C_{12}$alkyl may be methyl, ethyl, propyl, isopropyl, butyl, isobutyl or sec-butyl, as well as pentyl, hexyl, heptyl, octyl, nonyl, decyl, undecyl, dodecyl or the isomers thereof. $R_1$ is preferably a branched $C_4$–$C_{12}$alkyl group such as sec-butyl, 1-methylbutyl, 1-methylpentyl, 1-methylhexyl, 1-methyloctyl, 1-methylnonyl, 1-methyldecyl or 1-methylundecyl. The most preferred meaning of $R_1$ is sec-butyl.

$R_1$ as a phenyl-$C_1$–$C_3$alkyl radical is the benzyl, phenethyl or α,α-dimethylbenzyl radical.

The compounds of formula (1) obtainable by the process of this invention can be used for the photochemical stabilisation of natural and synthetic fibres (q.v. European patent application 0 112 120).

The invention is illustrated by the following Examples.

EXAMPLE 1

80.9 g of 2-(2'-hydroxy-3'-sec-butyl-5'-tert-butylphenyl)benzotriazole are added over 1 hour at 15°–20° C. to 150 ml of 25% oleum. The resultant solution is stirred for 16 hours at room temperature and then, with efficient stirring, poured into a mixture of 600 g of ice and 400 ml of water. The precipitated product is heated to 80° C. and, after cooling to room temperature, isolated by filtration. The acid is well squeezed out and then suspended in 1 liter of water. With stirring, the suspension is neutralised (pH 7) with 30% sodium hydroxide solution over 1½ hours. The dense crystal slurry is again heated to 80° C., whereupon a readily filterable crystalline product forms and is isolated by filtration after cooling to room temperature. The filter product is dried at 100° C. under vacuum, affording 83.5 g (90.4% of theory) of the compound of formula

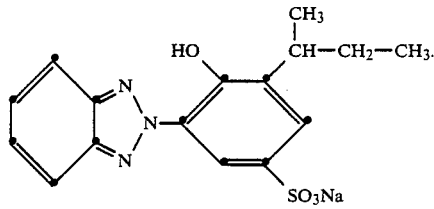

EXAMPLE 2

With stirring, 161.5 g of 2-(2'-hydroxy-3'-sec-butyl-5'-tertbutylphenyl)benzotriazole are added over 15 minutes to 640 g of sulfuric acid monohydrate, whereupon the temperature rises to 35° C. Under a low vacuum (117–143 mbar), the temperature is raised over 1 hour to 80° C. and stirring is continued for 4 hours at this temperature. After cooling to 60° C., the dark solution is poured into 2 liters of water of 50° C., whereupon the temperature rises to 85° C. The batch is stirred for 20 minutes at 80°–85° C., then cooled to room temperature, and the precipitated acid is isolated by filtration. The filter product is then suspended in 1 liter of water and the pH is adjusted to 7 with 30% sodium hydroxide solution. The sodium salt is isolated by filtration, washed with 400 ml of a 3% aqueous solution of sodium chloride, and dried at 80° C. under vacuum, affording 172 g (93.1% of theory) of the product of the formula as indicated in Example 1.

EXAMPLE 3

With stirring, 161.5 g of 2-(2'-hydroxy-3'-sec-butyl-5'-tertbutylphenyl)benzotriazole are added over 5 minutes to 350 ml of 92% sulfuric acid, whereupon the temperature rises from 20° to 26° C. The orange red solution is heated, under a low vacuum, to 80° C. over 90 minutes and stirred for 15 hours at this temperature. After cooling to 60° C., the solution is poured into a solution, heated to 50° C., of 100 g of sodium chloride in 2 liters of water, whereupon the temperature rises to 84° C. The batch is stirred for 15 minutes at this temperature and, after cooling to 40° C., the precipitated acid is isolated by filtration and suspended in 1 liter of water. The pH of the suspension is adjusted to 7 with 30% sodium hydroxide solution. The sodium salt is isolated by filtraton and washed with 400 ml of a 30% aqueous solution of sodium chloride and dried at 80° C. under vacuum, affording 168 g (92% of theory) of the product of the formula as indicated in Example 1.

What is claimed is:

1. A process for the preparation of a 3-]2'H-benzotriazol-2')-yl]-4-hydroxybenzenesulfonic acid, or a salt thereof, of formula

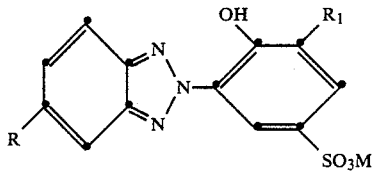

wherein
R is hydrogen or chlorine,
$R_1$ is sec-butyl, 1-methylbutyl, 1-methylpentyl, 1-methylhexyl, 1-methyloctyl, 1-methylnonyl, 1-methyldecyl or 1-methylundecyl and M is hydrogen, sodium or potassium, which process comprises sulfonating a 2-(2'-hydroxy-5'tert-butylphenyl)-benzotriazole of formula

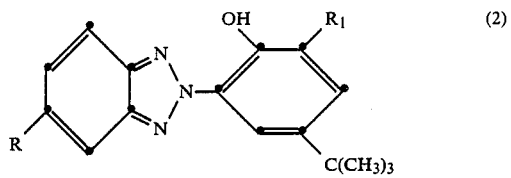

wherein R and $R_1$ are as defined above, with sulfuric acid, in which the tert-butyl group is replaced by the $SO_3H$ group with elimination of isobutylene, and neutralizing the final product to pH 7.

2. A process according to claim 1 for the preparation of a compound of the formula as indicated in claim 1, wherein R is hydrogen and $R_1$ is sec-butyl.

3. A process according to claim 1, wherein the sulfuric acid employed is 80–100% sulfuric acid or oleum having a content of up to 25% of free $SO_3$.

4. A process according to claim 1, wherein the sulfonation is carried out in the temperature range from 0° to 200° C.

5. A process according to claim 1, wherein the sulfonation is carried out under slightly reduced pressure.

* * * * *